United States Patent [19]

Ferrato et al.

[11] Patent Number: 4,879,061

[45] Date of Patent: Nov. 7, 1989

[54] LIQUID CRYSTALLINE MATERIALS AND METHOD OF MAKING SAME

[75] Inventors: Joseph P. Ferrato; Julie C. Ferrato, both of Akron, Ohio

[73] Assignee: Crystaloid Electronics Co., Hudson, Ohio

[21] Appl. No.: 912,918

[22] Filed: Sep. 29, 1986

[51] Int. Cl.$^4$ .................. C02F 1/13; C09E 19/30; C07C 121.60; C07C 121/48; C07C 13/28; C07C 49/313; C07C 49/702

[52] U.S. Cl. .................. 252/299.62; 252/299.5; 358/350 R; 558/419; 558/411; 558/423; 558/425; 558/426; 558/420; 558/421; 568/631; 568/642; 568/570; 570/129; 570/182; 585/20; 585/25

[58] Field of Search .................. 252/299.63, 299.5; 350/350 R; 558/419, 420, 421, 423, 425, 411, 426; 568/642, 644, 645, 647, 631; 570/129, 182; 585/20, 25

[56] References Cited

U.S. PATENT DOCUMENTS

| | | | |
|---|---|---|---|
| 4,130,502 | 12/1978 | Eidenschink et al. | 252/299.63 |
| 4,154,697 | 5/1979 | Eidenschink et al. | 252/299.63 |
| 4,198,130 | 4/1980 | Boller et al. | 252/299.63 |
| 4,330,426 | 5/1982 | Eidenschink et al. | 252/299.63 |
| 4,331,552 | 5/1982 | Eidenschink et al. | 252/299.63 |
| 4,406,814 | 9/1983 | Ferrato | 252/299.63 |
| 4,415,470 | 11/1983 | Eidenschink et al. | 252/299.63 |
| 4,419,264 | 12/1983 | Eidenschink et al. | 252/299.63 |
| 4,432,885 | 2/1984 | Petrzilka et al. | 252/299.62 |
| 4,478,740 | 10/1984 | Eidenschink et al. | 252/299.63 |
| 4,490,305 | 12/1984 | Eidenschink et al. | 252/299.63 |
| 4,510,069 | 4/1985 | Eidenschink et al. | 252/299.63 |
| 4,536,021 | 8/1985 | Sugimori et al. | 252/299.63 |
| 4,600,528 | 7/1986 | Eidenschink et al. | 252/299.62 |
| 4,627,933 | 12/1986 | Eidenschink et al. | 252/299.65 |
| 4,629,581 | 12/1986 | Boller et al. | 252/299.63 |
| 4,659,499 | 4/1987 | Ferrato | 252/299.63 |

FOREIGN PATENT DOCUMENTS

| | | | |
|---|---|---|---|
| 2636684 | 2/1978 | Fed. Rep. of Germany | 252/299.63 |
| 59-42329 | 3/1984 | Japan | 252/299.63 |
| 59-44330 | 3/1984 | Japan | 252/299.63 |
| 8605486 | 9/1986 | World Int. Prop. O. | 252/299.63 |

*Primary Examiner*—Teddy S. Gron
*Attorney, Agent, or Firm*—Oldham & Oldham Co.

[57] ABSTRACT

A method of making liquid crystalline compounds of the formula

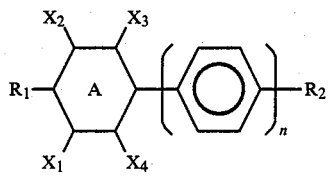

where A represents a cyclohexane ring, n has values of 1, 2 or 3, $R_1$ is an alkyl radical, $R_2$ is an alkyl, alkoxy, or alkylcyclohexyl or cyanide radical, and $X_1$ is lower alkyl and $X_2$, $X_3$ and $X_4$ is alkyl and preferably methyl, ethyl or propyl, hydrogen, halogen and preferably fluorine or cyanide and to the compound.

13 Claims, No Drawings

LIQUID CRYSTALLINE MATERIALS AND METHOD OF MAKING SAME

TECHNICAL FIELD

This invention relates to liquid crystalline materials that generally are more stable and have satisfactory viscosities. More particularly, this invention relates to a family of liquid crystalline materials having satisfactory optical display characteristics and stability and to a method of preparing said materials. Also, this family of liquid crystalline materials have better order parameters and can be used with dyes alone or in guest host systems to advantage.

BACKGROUND ART

Derivatives of benzene and biphenyl have been used as liquid crystals and these U.S. Pat. Nos. such as 4,130,502; 4,330,426 and 4,331,552 illustrate these types of the benzene and biphenyl derivatives. These liquid crystals have, relatively speaking, high viscosities. Another U.S. Pat. No. 4,406,814 uses an ester of cyclohexanoic acid as liquid crystals to get lower viscosities but these viscosities are still higher than desired in many cases. Also, the ester group is susceptible to hydrolysis so they have a degree of instability.

Thus, the patents mentioned above are characterized in one aspect as having essentially 4,4' substitution in the cyclic rings such as benzene, biphenyl or cyclohexane whereas U.S. 4,406,814 is the exception as it teaches the use of substituents in the other position of the cyclohexane ring.

DISCLOSURE OF INVENTION

A principle aspect of this invention is to disclose a family of novel liquid crystalline or potentially liquid crystalline compounds characterized by being chemically stable and having low viscosities and being mixable with other crystalline liquid compounds to give lower viscosity mixtures.

Representative examples of the liquid crystalline materials of this invention are those having the structure

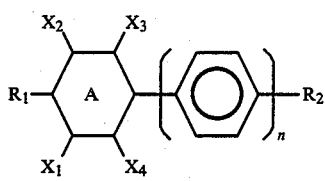 (1)

where A designates a cyclohexyl ring, n has the value of 1, 2 or 3 and preferably 1 or 2, $R_1$ is an alkyl radical up to 18 or more, usually 2 to 12, preferably 4, 5 or 6 carbon atoms, $R_2$ is alkyl or alkoxy, alkylcyclohexyl radical or cyanide group and $X_1$, $X_2$, $X_3$ and $X_4$ is lower alkyl and preferably methyl or ethyl, halogen, preferably fluorine and cyano but preferably hydrogen whereby no more than 2 or 3 and preferably only one of the $X_2$, $X_3$ and $X_4$ radicals is other than hydrogen. Thus, substituted p-alkyl or p-alkoxy phenyl or biphenyl-1-alkylcyclohexanes can be made where nonpara-substituted on the alkyl cyclohexane is methyl or ethyl and related alkyl radicals, halogen or cyano radicals.

The materials of this invention in one embodiment can be made by converting to an alkyl group the carboxylic group attached to the cyclohexane ring of the compositions shown by the formula as follows:

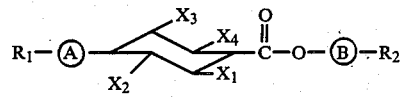

The above equation is from claim 1 of U.S. Pat. No. 4,406,814 where the symbols have values given therein, and the groups appended to the cyclohexane ring are preferably equatorial with respect thereto. Although they may be either trans- or cis- relative to the equatorial axis.

The nature of this invention and its benefits and advantages may be more readily seen and understood by the following representative and exemplifying examples wherein all parts and percentages are by weight unless otherwist indicated.

The representative cyclohexanoic acid components of the composition of U.S. Pat. No. 4,406,814 such as 4(4'alkylphenyl)-2-alkyl cyclohexanoic acid, 4(4'-alkoxyphenyl)-2-alkyl cyclohexanoic acid or 4(4'-alkylbiphenyl)-2-alkyl cyclohexanoic acid can be treated to form the compounds of this invention. Also, the alkoxy derivative may be used and the $X_1$ to $X_4$ group or groups can be alkyl, preferably 1 to 3 carbon atoms, halogen, preferably fluorine and cyano.

In one procedure, the precursors of the above-described cyclohexanoic acid compounds, such as those of the formula

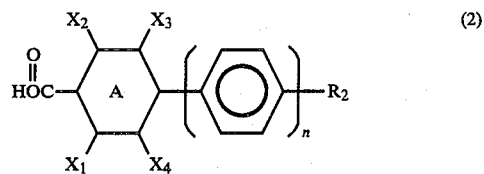 (2)

where the symbols have the values given above for Formula 1, can be chlorinated by treatment with phosphorus pentachloride as taught in U.S. Pat. No. 4,406,814 or other well known method to yield the corresponding acid chloride compound.

EXAMPLE 1

Preparation of Ketone Derivative From The Acid Chloride

An acid chloride of the substituted cyclohexanoic acid, any of the compounds of Formula 2, or those available from U.S. Pat. No. 4,406,814 can be converted to the ketone form by treating each mole of said acid chloride with 2 moles of alkyl lithium. Thus, if the alkyl lithium is propyl, butyl, amyl or higher alkyls such as decyl or octadecyl, the cyclohexanoic acid will be converted to the corresponding alkyl ketones of the cyclohexanoic acid, i.e., the propyl, butyl, amyl or decyl ketone derivative. Hence, by choice of proper alkyl lithiums, the number of carbon atoms in the alkyl radical portion of the ketone is controlled to the desired length.

These alkyl ketone derivatives are then treated to convert the carbonyl of the ketone to a methylene group to yield compositions of this invention, where the length of $R_2$ is increased by 1 carbon over the number in the alkyl lithium. For instance, the butyl ketone known as 4(4'-butoxyphenyl)-2-methyl cyclohexane is formed by treating the acid chloride of Example 1, i.e., 4(4'-butoxyphenyl)-2-methyl cyclohexanoic acid chloride with at least two moles of lithium butyl in an inert atmosphere.

EXAMPLE 2

A typical representative procedure for reducing the carbonyl is as follows.

Thirty-six grams of an all equatorial butyl ketone of 4(4'-butoxy phenyl)-2-methylcyclohexane, in a mixture of 1.2 liters of ethanol and 1.2 liters of diethylene glycol and 125 ml of hydrazine hydrate was refluxed with stirring for three hours. Then, the ethanol was allowed to boil off to cause the temperature in the reaction vessel to rise to 170° C. before 500 ml more of ethanol was added to cool the temperature of the reaction vessel. Then an admixture of 200 ml 55 percent hydrazine and 200 ml of ethanol was added and the resulting mixture was refluxed with stirring an hour before adding 56 grams of potassium hydroxide and continuing the refluxing for an additional half hour. At this point the ethanol was distilled off and the temperature of the reaction vessel was raised to 240° C. and allowed to reflux with stirring overnight. The next day, the cooled reaction mixture had 3 liters of water added thereto and then it was extracted three times with 200 ml of ligroin. The extract was washed three times with 200 ml of water and then dried over sodium sulfate.

The dry extract had the ligroin stripped off to leave a crude product which showed no ketone groups by infrared analysis. This crude product was dissolved in methylene chloride and passed through a silica gel chromatographic column and recrystallized three times from isopropyl alcohol to give 14 grams of white crystals of equatorial 4(4'butoxyphenyl)2-methyl-1-amyl cyclohexane.

NMR analysis using a crabon 13 standard showed one isomer, all equatorial and a melting point C→I of 28.5° and would not recrystallize at room temperature, i.e, 23° C. for several weeks.

In some respects, this 4(4'-butoxy-phenyl)1-amyl-2-methylcyclohexane acted like the so-called theoretical liquid crystals.

The above property of not readily recrystallizing and its properties shown in its mixture with other liquid crystals indicated it to have a theoretical N→I transition temperature of about 10° C. To show its usefulness, a 10 percent by weight blend of 4(4'-butoxyphenyl)-2-methyl-1-amylcyclohexane with 90 percent by weight of a liquid crystalline material available from Merck as ZL-1221 was made. This 10/90 percent blend was used to make a 7 micron optical test display device and a 100 percent of the ZL-1221 was used to make a second 7 micron optical test display device as a control. The optical test display devices were driven at the 5 volt level and the time on, $T_{on}$, and time off, $T_{off}$, in milliseconds was determined for these devices at room temperature and at minus 20° C.

The test data was as follows:

| Temperature Condition | Room | | −20° C. | |
|---|---|---|---|---|
| | Ton | Toff | Ton | Toff |
| 10/90 Blend | 28 | 56 | 800 | 1400 |
| 100% ZL-1221 | 52 | 56 | 1300 | 1400 |

The above 10 percent blend had a clear point of 77.5° C. and a viscosity of 14 cps. The ZL-1221 had a clear point of 90° C. and its 90 percent by weight blend with 10 percent heptylbiphenyl had a clear point of 66.3° C. and a viscosity of 26 cps.

This data demonstrates the crystalline compound, i.e., 4(4'-butoxyphenyl)-1-amyl-2-cyclohexane tested had a lower viscosity, lower clear point, a wider operating range than the current commercial material ZL-1221.

Thus, the compounds of Formula 1 are useful liquid crystalline materials.

Instead of the above butyl ketone, the propyl, amyl and related ketones of 4(4'-butoxy biphenyl)2-methyl cyclohexane may be used in the above procedure to reduce the carboxyl group to a methylene group to yield alkylated products of a low viscosity liquid crystalline material of the following formula

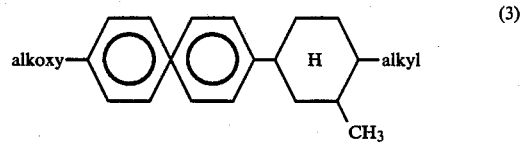
(3)

Alternatively, any of the starting compounds from U.S. Pat. No. 4,406,814 could be converted to the indicated ketone derivative as exemplified by equation 4.

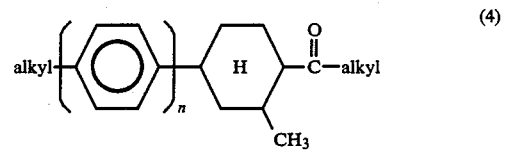
(4)

and upon reduction of the carbonyl group would yield

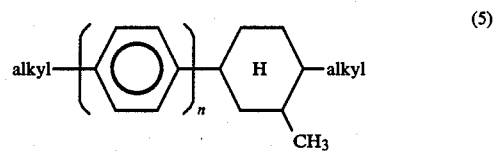
(5)

where the alkyl radical contains one or more carbon atoms than in the above acid chloride.

The above description and formula demonstrated the preparation of the cyclohexane derivatives where $X_1$ is methyl or hydrogen and $X_2$, $X_3$ and $X_4$ are hydrogen. It should be understood that by starting with the appropriate cyclohexanoic acid of Formula 2 where $X_1$, $X_2$, $X_3$ and $X_4$ has the desired radical value in the desired position or positions, cyclohexane derivatives of Formula 1 may be made where $X_1$, $X_2$, $X_3$ and $X_4$ have the values indicated for Formula 1.

Examples of other compositions that can be produced is shown by the following formula

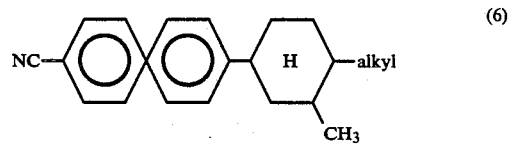
(6)

The cyclohexyl alkane derivatives above of Formulae 1 to 5 can be converted to the iodo derivative and then have the iodo group replaced by cyano to give cyanic derivatives thereof as represented in Formula 6. This preparation is shown in the following examples.

In a 12 liter flask equipped with a mechanical stirrer, condensor and heating mantle was charged 790 grams 1-amyl, 4-biphenyl cyclohexane, 2150 ml of acetic acid and 206 ml carbon tetrachloride having dissolved therein 262.9 gm of iodine followed by 490 ml of water and 103.1 gm of iodic acid and 77.3 ml of 98 percent sulfuric acid. The reaction was allowed to continue under reflux overnight. The reaction mixture was decolorized with a sufficient 10 percent aqueous solution of sodium bisulfite to just discharge the iodine color. The decolorized reaction mixture was extracted with 18 liters of methylene dichloride, the methylene dichloride extract was washed three times with water and dried with a drying agent. The methylene chloride was stripped away to give the crude product. The crude product was recrystallized twice from a 10–20 percent toluene isopropylacetate solution. The recrystallized product was dried at 80° C. in an oven. The resulting product, i.e., the 1-amyl, 4-(4'-iodobiphenyl) cyclohexane was obtained in a yield of 834 grams.

Similarly, the 2 or 3 substituted alkyl derivative of the above cyclohexane can be treated to yield the corresponding iodo compounds, for example, 1-amyl, 2-ethyl, 4-(4'-iodobiphenyl) cyclohexane or 1-amyl-3-methyl,4-(4'-iodobiphenyl) cyclohexane.

These iodo derivatives can be converted to the cyano derivative by its reaction with cuprious cyanide in a suitable solvent such as dimethylfuran as illustrated by the following representative and illustrative example.

1-amyl, 2-methyl, 4-(4'-iodobiphenyl) cyclohexane (1735 parts) is placed in a suitable reactor equipped with a mechanical stirrer and condensor together with 6500 parts of diemthylfuran. The vapors from the condensor is passed to a trap to destroy any free cyanide therein as cyanide is poisonous. Then, 415 parts of cuprious cyanide is added and the mixture is allowed to reflux overnight or a relatively long time. The reaction product is treated with about 9000 parts of toluene and 1344 ml of 25 percent aqueous ammonium hydroxide. If no phase separation occurs, water is added to achieve the desired separation of the toluene/dimethylfuran. This separated phase is washed three times with large amounts of 5 percent aqueous ammonium hydroxide, then it is washed three times with water, followed in succession by three 5 percent aqueous hydrochloric acid washes and three water washes. The solvent is removed to give a crude yield of about 1000 or more parts of the cyanide derivative. The crude product may be purified by recrystallizing three times in isopropylacetate at the appropriate freezer temperature. Thus, these examples provide a way to make the cyanide derivatives such as 1-alkyl, 2 or 3-alkyl,4-(4'-cyanobiphenyl) cyclohexane where the alkyl radical may have any of the usual values but those in the 2 or 3 position of the cyclohexane ring are preferably methyl and ethyl whereas the one in the one position preferably has four or more carbon atoms. Also, those of ordinary skill in the art can readily see how the Gringard reaction can be used to make some of the compounds of this invention, for instance the halogen and cyanide compounds.

In addition to providing a novel family of liquid or so-called potentially crystalline materials when mixed amongst themselves within the family or when mixed with other liquid crystalline materials, the family of liquid crystalline materials of the invention may be used as a host with positive dichroic dyes such as representative anthraquinones in an amount preferably from 0.5 percent to about 10 percent by weight of the dye to the weight of the host to provide negative image optical displays. The members of the family of liquid crystalline materials may be used as a host with dye having a negative optical axis such as where members of the family of liquid crystalline materials of the invention are mixed with tetrazene in an amount preferably from 1 percent to about 40 percent by weight of tetrazene to the weight of the host.

Members of the family of liquid crystalline materials are also able to exhibit electrical frequency dependency by having the capability of changing from a material having positive dielectric anisotrophy to a material having negative dielectric anistrophy as a result of changing the frequency of the electrical field imposed across the materials.

Examples of other liquid crystalline materials particularly useful for mixing with one or more members of the family of liquid crystalline materials of the invention have the following formulas:

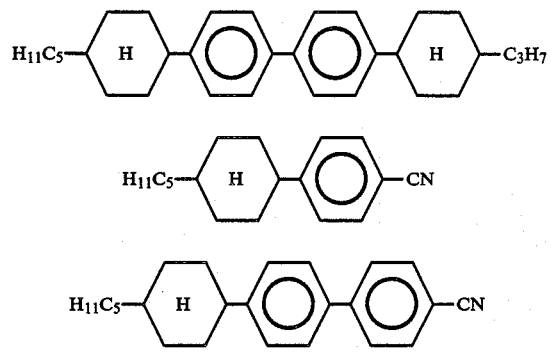

While in accordance with the patent statutes only the best mode and preferred embodiment of the invention has been illustrated and described in detail, it is to be understood that the invention is not limited thereto or thereby, but that the scope of the invention is defined by the appended claims.

What is claimed is:

1. A liquid crystalline compound having the formula:

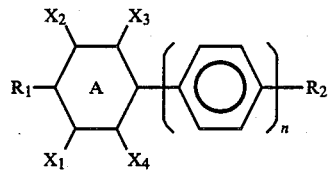

where A designates a cyclohexane ring, n has values of 1, 2 or 3, $R_1$ is an alkyl radical, $R_2$ is an alkyl, alkoxy, or alkylcyclohexyl radical or cyanide with at least one of the $X_1$, $X_2$, $X_3$ and $X_4$ groups being selected from the class of alkyl, halide and cyanide and the rest of the $X_1$, $X_2$, $X_3$ and $X_4$ groups are selected from hydrogen.

2. The compound of the formula of claim 1 wherein $R_1$ is an alkyl radical having up to 18 carbon atoms.

3. The compound of the formula of claim 1 wherein $R_2$ is a cyanide radical.

4. The compound of the formula of claim 1 wherein $R_2$ is alkyl.

5. The compound of the formula of claim 1 wherein n is 1.

6. The compound of the formula of claim 1 where the group

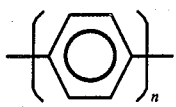

is biphenyl.

7. The compound of the formula of claim 1 wherein $R_2$ is an alkoxy group.

8. The compound of the formula of claim 1 wherein $R_2$ is an alkyl cyclohexyl group and the alkyl portion contains 1 or more carbon atoms.

9. The compound of the formula of claim 1 wherein at least one of $X_1$, $X_2$, $X_3$ or $X_4$ is alkyl.

10. The compound of the formula of claim 1 wherein at least one of $X_1$, $X_2$, $X_3$ or $X_4$ is fluoride and the rest are hydrogen or an alkyl.

11. The compound of the formula of claim 1 where n is 2 and $X_1$ is lower alkyl.

12. The compound of claim 1 wherein n is 1, $X_1$ is alkyl, and $X_2$, $X_3$ and $X_4$ are hydrogen and $R_2$ is alkyl.

13. The compound of claim 1 where one of $X_1$, $X_2$, and $X_3$ and $X_4$ is alkyl and $R_2$ is cyanide.

* * * * *